United States Patent
Oba et al.

(10) Patent No.: US 8,722,173 B2
(45) Date of Patent: May 13, 2014

(54) LIQUID-PERVIOUS FIBROUS NON-WOVEN FABRIC

(75) Inventors: Toru Oba, Kanonji (JP); Satoshi Mizutani, Kanonji (JP); Akihiro Kimura, Kanonji (JP)

(73) Assignee: Unicharm Corporation, Shikokuchuo-Shi, Ehime (JP)

(*) Notice: Subject to any disclaimer, the term of this patent is extended or adjusted under 35 U.S.C. 154(b) by 173 days.

(21) Appl. No.: 13/266,923

(22) PCT Filed: Apr. 26, 2010

(86) PCT No.: PCT/JP2010/057373
§ 371 (c)(1),
(2), (4) Date: Oct. 28, 2011

(87) PCT Pub. No.: WO2010/131565
PCT Pub. Date: Nov. 18, 2010

(65) Prior Publication Data
US 2012/0045620 A1    Feb. 23, 2012

(30) Foreign Application Priority Data

May 14, 2009 (JP) ................................. 2009-117994
Apr. 16, 2010 (JP) ................................. 2010-095411

(51) Int. Cl.
*B32B 3/30* (2006.01)
*B32B 5/14* (2006.01)
*A61F 13/15* (2006.01)
*D04H 3/00* (2012.01)
*D04H 13/00* (2006.01)
*B27N 3/12* (2006.01)
*B31F 1/07* (2006.01)

(52) U.S. Cl.
USPC ........... 428/167; 428/171; 428/212; 604/367; 604/385.01; 442/334; 264/257; 264/546; 156/209

(58) Field of Classification Search
USPC ............ 428/167, 170, 171, 212; 604/385.01, 604/367; 156/209; 264/257, 546; 442/334, 442/408
See application file for complete search history.

(56) References Cited

U.S. PATENT DOCUMENTS 3,746,607 A * 7/1973 Harmon et al. ................ 428/167
2007/0298214 A1  12/2007 Noda et al.
(Continued)

FOREIGN PATENT DOCUMENTS

EP    2034069 A1    3/2009
EP    2039818 A1    3/2009
(Continued)

OTHER PUBLICATIONS

International Search Report for PCT/JP2010/057373 mailed Jun. 15, 2010.

(Continued)

*Primary Examiner* — Donald J Loney
(74) *Attorney, Agent, or Firm* — Lowe Hauptman & Ham, LLP

(57) ABSTRACT

A liquid-pervious fibrous non-woven fabric includes staple fibers made of thermoplastic synthetic resin fused together which is formed on its upper surface with a plurality of ridges, and a plurality of grooves extending in parallel in a longitudinal direction. The ridges and grooves are arranged alternately in a transverse direction. On the upper surface, some of the staple fibers extend across the ridges to the adjacent grooves on each side of the ridges and are, in the respective grooves, fused to the staple fibers of a different type from the former staple fibers.

11 Claims, 6 Drawing Sheets

(56) References Cited

U.S. PATENT DOCUMENTS

| | | |
|---|---|---|
| 2007/0298671 A1 | 12/2007 | Noda et al. |
| 2008/0010795 A1 | 1/2008 | Mizutani et al. |
| 2008/0044622 A1 | 2/2008 | Noda et al. |
| 2008/0044628 A1 | 2/2008 | Noda et al. |
| 2008/0045915 A1 | 2/2008 | Noda et al. |

FOREIGN PATENT DOCUMENTS

| | | | |
|---|---|---|---|
| EP | 2161361 | A1 | 3/2010 |
| JP | 2008-002034 | A | 1/2008 |
| JP | 2009-030218 | A | 2/2009 |
| WO | 2008152999 | A1 | 12/2008 |
| WO | 2008156075 | A1 | 12/2008 |
| WO | 2009001590 | A1 | 12/2008 |

OTHER PUBLICATIONS

Extended European Search Report corresponding to EP 10774823.8, dated Nov. 5, 2012.

* cited by examiner

FIG.6
(a)
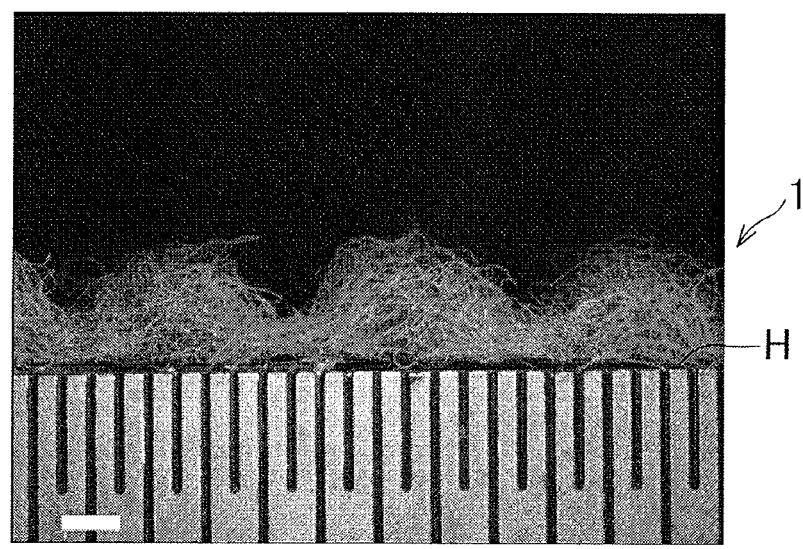
(b)
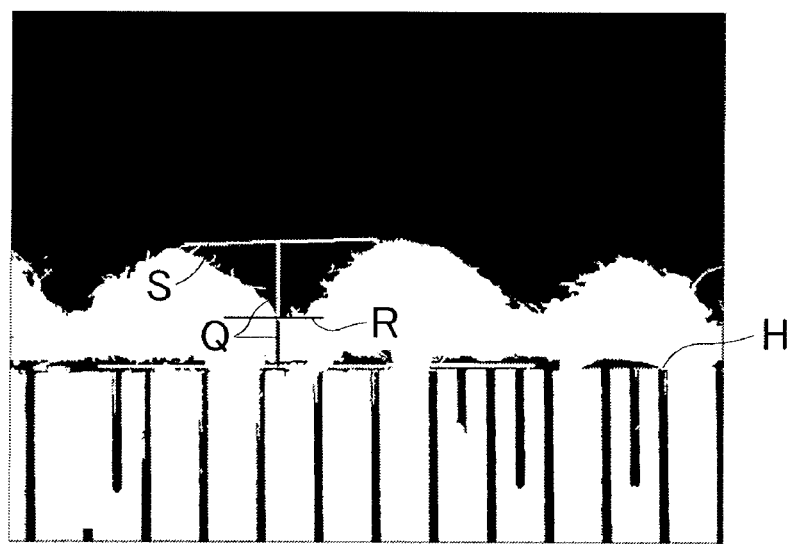

LIQUID-PERVIOUS FIBROUS NON-WOVEN FABRIC

RELATED APPLICATIONS

The present application is a National Phase of International Application Number PCT/JP2010/057373, filed Apr. 26, 2010 and claims priority from, Japanese Application Number 2009-117994, filed May 14, 2009, and Japanese Application Number 2010-095411, filed Apr. 16, 2010.

TECHNICAL FIELD

The present invention generally relates to liquid-pervious fibrous non-woven fabrics and particularly to fibrous non-woven fabrics being suitable to be used as top-sheets for bodily fluid-absorbent articles such as disposable diapers or menstruation napkins.

BACKGROUND OF INVENTION

Liquid-pervious fibrous non-woven fabrics formed of staple fibers of thermoplastic synthetic resin are known. For example, a non-woven fabric disclosed in JP 2009-30218 A (PTL 1) is formed on the upper surface thereof with a plurality of ridges and grooves spaced one from another in a machine direction and alternately extending in parallel with one another in a cross direction orthogonal to the machine direction. The lower surface thereof is substantially flat.

CITATION LIST

Patent Literature

{PTL 1} JP 2009-30218 A

SUMMARY OF INVENTION

Technical Problem

The non-woven fabric described in PTL 1 is made by a method including a step of transporting a fibrous web loaded on a mesh-plate in the machine direction while the upper surface of the fibrous web is subjected to hot air jets supplied from a plurality of nozzles arranged at a predetermined pitch in the cross direction. In the course of this step, the fibrous web is formed with the grooves directly below the nozzle and formed with the ridges directly below a space defined between each pair of the adjacent nozzles. In this non-woven fabric of prior art, each of the grooves has a level of density sufficiently higher than that of each of the ridges to assure that bodily fluids may rapidly move from the ridges to the grooves when this non-woven fabric is used as the top-sheet covering a bodily fluid-absorbent core. However, it is difficult for such grooves to let viscous bodily fluid such as menstrual blood smoothly pass through the top-sheet and the viscous bodily fluid is apt to dwell on the surface of the groove's bottom.

An object of the present invention is to improve the liquid-pervious fibrous non-woven fabric of prior art so that even viscous bodily fluid can quickly permeate the groove of the top-sheet.

Solution to Problem

According to the present invention, there is provided a liquid-pervious fibrous non-woven fabric having a longitudinal direction, a transverse direction and a thickness direction being orthogonal to one another and including upper and lower surfaces opposed to each other in the thickness direction and both extending in the longitudinal direction and the transverse direction, the upper surface being formed with ridges and grooves extending in parallel in the longitudinal direction to be alternately arranged in the transverse direction, the lower surface being substantially flat and staple fibers, made of thermoplastic synthetic resin, being fused together in the liquid-pervious fibrous non-woven fabric.

The present invention is characterized in that a thickness t measured from the lower surface to a bottom of each groove is in a range of 40 to 60% of a thickness T measured from the lower surface to an apex of each ridge and the staple fibers used to form the liquid-pervious fibrous non-woven fabric each having a fiber length sufficiently long to extend across at least one ridge to the grooves on both sides of the one ridge.

According to one embodiment of the present invention, the staple fibers extending across the ridges are fused, in each of the grooves adjacent to the ridges, with staple fibers of a different type from the staple fibers extending across the ridges.

According to another embodiment of the present invention, the liquid-pervious fibrous non-woven fabric has a mass in a range of 15 to 35 g/m$^2$.

According to still another embodiment of the present invention, a specific volume of the ridges is in a range of 70 to 105 cc/g and a specific volume of the groove is in a range of 40 to 60 cc/g.

According to yet another embodiment of the present invention, the staple fibers include those having an apparent fiber length in a range of 10 to 80 mm.

According to further another embodiment of the present invention, the ridges and the grooves are formed by subjecting a fibrous web containing a given mass/m$^2$ of the staple fibers made of the thermoplastic synthetic resin to hot air jets ejected from a plurality of nozzles arranged intermittently in a cross direction orthogonal to a machine direction while the fibrous web is continuously transported in the machine direction so that the ridge is formed directly below a space defined between each pair of the adjacent nozzles and the groove is formed directly below the nozzle.

Advantageous Effects of Invention

The liquid-pervious fibrous non-woven fabric according to the present invention contains the staple fibers extending across the ridges to the adjacent grooves on each side of the ridges and fused, in the respective grooves, with the staple fibers of the different type from the formers. Consequentially, even if the surface of the fibrous non-woven fabric comes in contact with the wearer's skin and the ridges are rubbed by the wearer's skin, fluffing possibly occurring on the surfaces of the ridges can be reliably restricted. The thickness t of each groove is maintained at a level of 40 to 60% of the thickness T of each ridge and therefore the liquid-pervious fibrous non-woven fabric is only slightly compressed in comparison with each ridge and there is no remarkable differential in specific volume between the ridge and the groove. Consequently, even viscous bodily fluids such as menstrual blood can rapidly permeate the fibrous non-woven fabric in the ridge as well as in the groove.

BRIEF DESCRIPTION OF DRAWINGS

FIGS. 6(a) and 6(b) are photographs exemplarily showing a cross-sectional shape of the liquid-pervious fibrous non-woven fabric.

DESCRIPTION OF EMBODIMENTS

Details of a liquid-pervious fibrous non-woven fabric according to the present invention will be more fully understood from the following description given hereunder with reference to the accompanying drawings.

Figure 1:
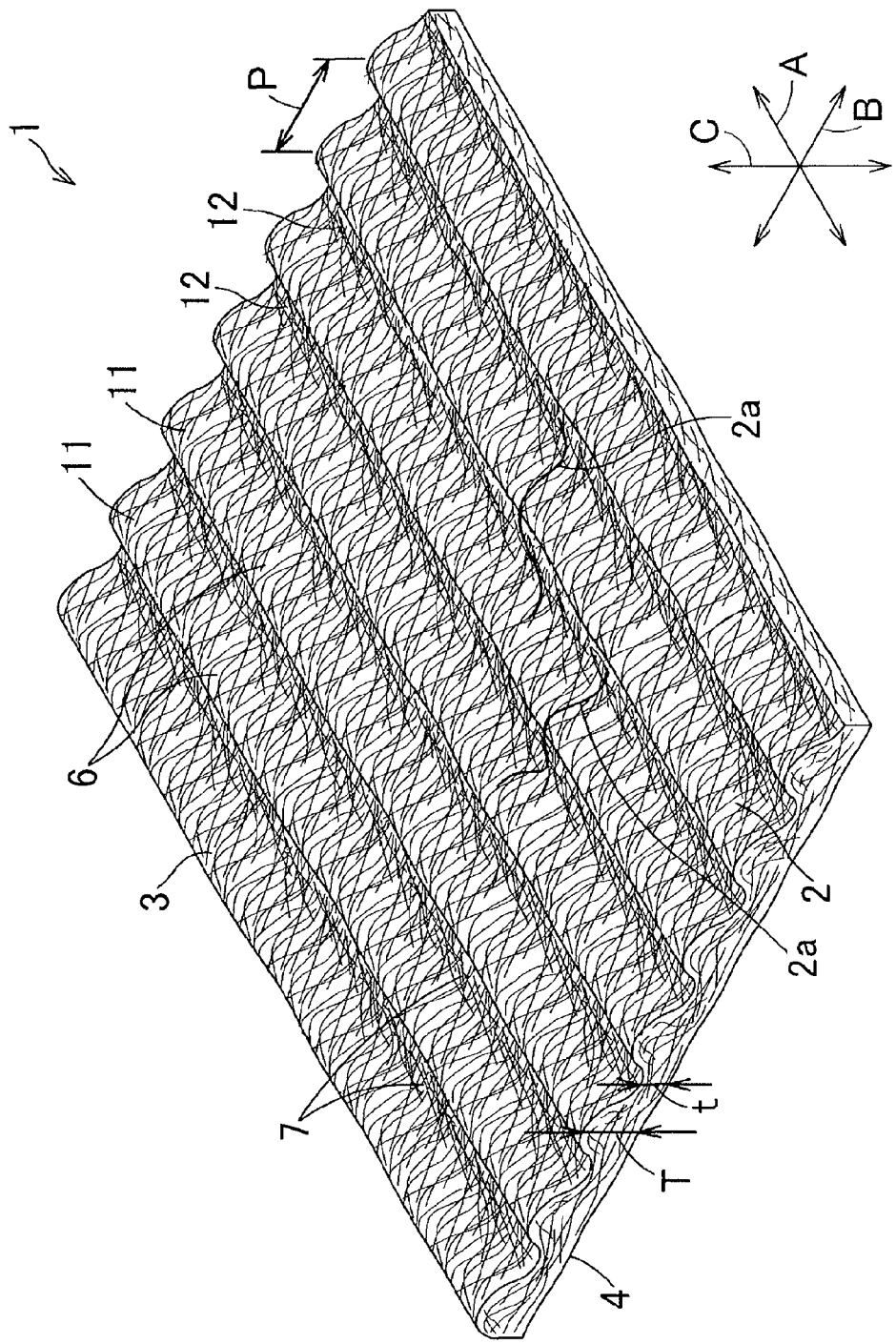
FIG. 1 is a perspective view of a liquid-pervious fibrous non-woven fabric.

Referring to FIG. 1 illustrating a perspective view of a liquid-pervious fibrous non-woven fabric 1, a liquid-pervious fibrous non-woven fabric 1 is formed by fusing together staple fibers 2 of thermoplastic synthetic resin and has a longitudinal direction A, a transverse direction B and a thickness direction C which are orthogonal to one another. As viewed in the thickness direction C, the non-woven fabric 1 has an upper surface 3 and a lower surface 4 opposed to each other wherein these surfaces 3, 4 extend in the longitudinal direction A and the transverse direction B. The non-woven fabric 1 is formed on the upper surface 3 with a plurality of ridges 6 and a plurality of grooves 7 wherein these ridges and grooves 6, 7 extend in parallel with one another in the longitudinal direction A to be arranged alternately in the transverse direction B. The lower surface 4 is substantially flat.

Each of the ridges 6 has, on its upper surface 3, an apex 11 located at the maximum height measured from the lower surface 4 and a thickness T from the lower surface 4 to this apex 11 is substantially constant across all the ridges 6. Pitches P, each defined by a distance between each pair of the adjacent apices 11, at which the ridges 6 are repetitively formed in the transverse direction B are substantially constant across the full width of the non-woven fabric 1.

Each of the grooves 7 has a bottom 12 located at the minimum height measured from the lower surface 4 and a thickness t from the lower surface 4 to the bottom 12, i.e., a height of the bottom 12 is substantially constant across all the grooves 7. Pitches, each defined by a distance between each pair of the adjacent bottoms 12, at which the grooves 7 are repetitively formed in the transverse direction B are the same as the pitches P and are substantially constant across the full width of the non-woven fabric 1.

The fibrous non-woven fabric 1 is suitable to be applied to liquid-pervious top-sheets in bodily fluid-absorbent articles such as disposable diapers, menstruation napkins or incontinent briefs. The top-sheet of the bodily fluid-absorbent article is adapted to cover a bodily fluid-absorbent core and used on the assumption that the top-sheet comes in contact with the wearer's skin. As the staple fibers 2 forming such fibrous non-woven fabric 1, thermoplastic synthetic fibers each having a fineness in a range of 1 to 8 dtex and an apparent fiber length in a range of 10 to 80 mm is used after the fibers have been modified to become hydrophilic. The apparent fiber length herein referred to is the value measured pursuant to Section 8.4, c) of Japanese Industrial Standards (JIS) L1015: 1999. It should be noted that the staple fibers 2 are fed into a carding machine as exemplarily illustrated in FIGS. 2 and 5 and, before fed into the carding machine, the staple fibers have already been subject to necessary treatments such as crimping. The staple fibers 2 collected for the measurement were substantially straightened on a stationary scale in a careful manner so that no tensile force might be exerted thereupon. In order to ensure that some of the staple fibers 2 can be fused together at a relatively low temperature and the fibrous non-woven fabric can be provided with an appropriate elastic recovery force against the compression deformation of the fibrous non-woven fabric in the thickness direction, preferably conjugated staple fibers may be used. Such conjugate staple fibers may be of side-by-side type or of core-in-sheath type and, in the core-in-sheath type, the sheath component may be a thermoplastic synthetic resin such as polyethylene having a relatively low melting temperature and the core component may be a thermoplastic synthetic resin such as polypropylene or polyester having a melting temperature higher than that of the sheath component.

The fibrous non-woven fabric 1 has a uniform mass per unit square meter and specifically in a range of 15 to 35 g/m². Each of the ridges 6 has the thickness T in a range of 0.5 to 5 mm and a plurality of the ridges 6 are arranged at the pitch P in a range of 2 to 8 mm. Each of the grooves 7 has the thickness t corresponding to 25 to 60% of the thickness T. Of the staple fibers 2 on the upper surface 3 of the fibrous non-woven fabric 1, some of the staple fibers 2 extend from at least one of the grooves 7 to the adjacent groove 7 across at least one ridge 6 lying between these two adjacent grooves 7. Some of the staple fibers are exaggerated in thickness as denoted by reference numerals 2a in FIG. 1. While some of the staple fibers 2 are mechanically entangled together and fused together, the staple fibers extending on the upper surface 3 like the staple fibers 2a are fused with the other staple fibers 2 entangling with these staple fibers 2a in the adjacent grooves 7, particularly on the respective bottoms 12 of these adjacent grooves 7. In this case, fluffing of the staple fibers 2 in the ridges 6 is restricted even if the apices 11 of the ridges 6 defined between each pair of the adjacent grooves 7 is rubbed by the wearer's skin. Additionally, since the staple fibers 2 are fused together at the bottoms 12 of the grooves 7 in which the wearer's skin apt not to contact with the upper surface 3, such fused regions are prevented from causing irritation against the wearer's skin. Fluffing on the upper surface 3 would make the upper surface 3 rough to the touch and/or allow bodily fluids such as menstrual blood to stay behind on the upper surface 3. However, the feature of the staple fibers 2a effectively eliminates such an undesirable possibility. To ensure that the staple fibers 2a reliably function in the expected manner, it is desirable for the staple fibers 2a to have the apparent fiber length sufficient to extend from at least one groove 7 to the other groove 7 adjacent to the one groove 7. In other words, it is desirable for the staple fibers 2a to have the apparent fiber length larger than the pitch P, and preferably twice larger than the pitch P. This is irrespective of whether the staple fibers 2a extend to describe, for example, a spiral shape or to describe a zigzag shape.

Figure 2:
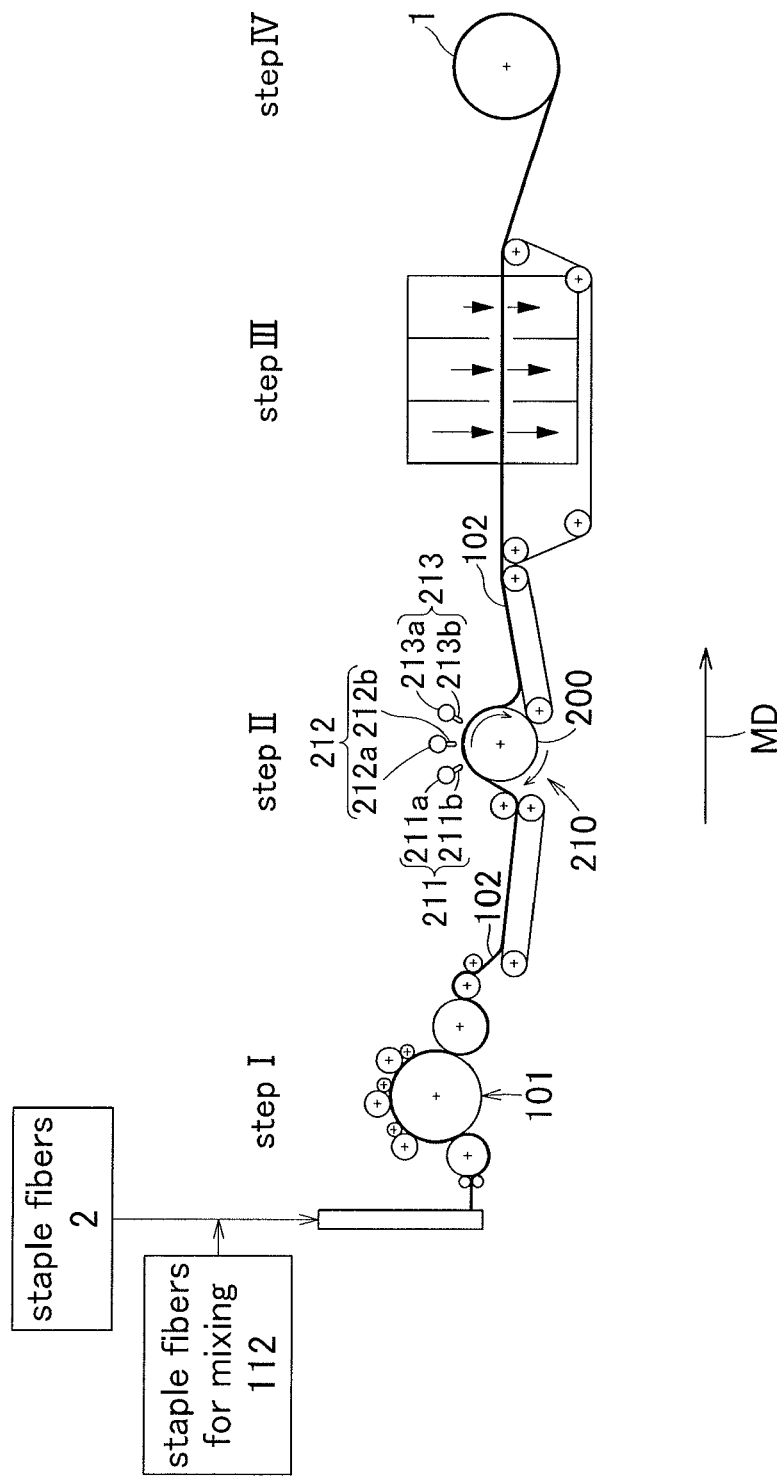
FIG. 2 is a diagram exemplarily illustrating one embodiment of the process for making the liquid-pervious fibrous non-woven fabric.

Referring to FIG. 2 exemplarily illustrating a process of making the fibrous non-woven fabric 1, in the step I, an assembly of the staple fibers 2 is opened by a carding machine 101 to obtain a fibrous web 102. On upstream of the carding machine 101, it is also possible to mix the staple fibers 2 with appropriate staple fibers 112 for mixing. In order to help the opening treatment by the carding machine 101, the staple fibers 2 are preferably provided with a mechanical crimp in advance. As the staple fibers 112 for mixing, the staple fibers different from the staple fibers 2 in type of thermoplastic synthetic resin or in fiber length or fineness may be used. The staple fibers 112 for mixing are used within the range of 40% by mass of the mass/m² of the fibrous web 102.

In the step II, the fibrous web is treated by hot air jets from an ejecting apparatus 210. The ejecting apparatus 210 serves to form the fibrous non-woven fabric 1 with the ridges 6 and the grooves 7 and includes a rotary suction drum 200 and a series of first nozzles 211, a series of second nozzles 212 and a series of third nozzles 213 for ejection of the hot air jets. The series of first, second and third nozzles (hereinafter referred to as "first, second and third nozzle assemblies") 211, 212, 213 respectively include first, second and third stationary manifolds 211a, 212a, 213a, and nozzles 211b, 212b, 213b. The first, second and third stationary manifolds 211a, 212a, 213a extend in an axial direction, i.e., in a cross direction CD (See FIG. 3) orthogonal to the machine direction MD and arranged at predetermined intervals in a circumferential direction of the rotary suction drum 200. The first nozzles 211b, 212b, 213b are respectively provided to the first, second and third stationary manifolds 211a, 212a, 213a at predetermined pitch in the cross direction CD to be spaced apart from the peripheral wall of the rotary suction drum 200 by a predetermined dimension. By way of example, in the first, second and third nozzle assemblies 211, 212, 213, the first, second and third individual nozzles 211b, 212b, 213b may be arranged at predetermined pitch, for example at 4 mm, in the cross direction CD to fall into lines in the machine direction MD. The first, second and third nozzle assemblies 211, 212, 213 are respectively adapted to eject the hot air jets at predetermined temperatures at predetermined flow rates from the respective nozzles 211b, 212b, 213b. As the first, second and third nozzles 211b, 212b, 213b, those having bore diameter in a range of 0.5 to 2.5 mm may be used.

The rotary suction drum 200 has its peripheral wall formed with a plurality of perforations 223 (See FIG. 4) uniformly distributed and these perforations 223 are in fluid-communication with a suction mechanism (not shown) for the rotary suction drum 200. For example, the peripheral wall may be formed with the perforations 223 each having a diameter in a range of 0.2 to 1 mm at an open area ratio of 15 to 30%. A circumferential velocity of the rotary suction drum 200 corresponds to a transport velocity of the fibrous web 102.

In the step II, prior to treatment of the fibrous web 2 by the hot air jets ejected from the third nozzle assembly 213, the hot air jets ejected from the first and second nozzle assemblies 211, 212 are applied to the fibrous web 102 in order to compress the fibrous web 102 being in a bulky state immediately after leaving the carding machine 101 and to smooth the surface of the fibrous web 102. More specifically, the temperature and pressure of the hot air jets ejected from the first and second nozzle assemblies 211, 212 are set to ensure that the staple fibers 2, 112 are softened but not fused and the staple fibers 2, 112 softened in this manner are compressed under the ejection pressure of the hot air jets until the thickness of the fibrous web 102 is reduced to ½ to ¼ of its initial thickness. In addition, after this treatment, surfaces of the fibrous web 102 become smooth. The temperature and pressure of the hot air jets ejected from the third nozzle assembly 213 is regulated so that the fibrous web 102 already compressed and smoothed may be now formed with the grooves 7 and at the same time the staple fibers 2 being present in the grooves 7 may be at least partially fused together.

In the step II, the hot air jets ejected from the first and second nozzles 211, 212 serves to smooth irregularities of the surface of the fibrous web 102 due to various factors such as fluffing of the staple fibers 2 and to provide the fibrous web 102 having a comfortably smooth surface. The hot air jets ejected from the third nozzle assembly 213 compresses the portions of the fibrous web 102 located directly below the respective third individual nozzles 213b to form the grooves 7 on the fibrous non-woven fabric 1 and simultaneously forms the respective portions directly below the respective spaces defined between each pair of the adjacent third individual nozzles 213b with the ridges 6. In view of the fact that the fibrous web 102 has been smoothed under the effect of the hot air jets ejected from the first and second nozzle assemblies 211, 212 before the ridges 6 are formed, the thickness of the ridges 6 measured from the lower surface of the fibrous web 102 is substantially uniform. This is true for the grooves 7 and a depth, i.e., a dimension of the grooves 7 measured from the lower surface of the fibrous web 102 is substantially uniform for the same reason. The fibrous web 102 having left the step II is conveyed by a mesh belt in the machine direction MD.

In the step III, the fibrous web 102 is subjected to the hot air jets set to a sufficiently high temperature to fuse the surfaces of the staple fibers 2 and thereby to fuse the staple fibers 2 together or the staple fibers 2 with the staple fibers 112 for mixing. In this way, the rub-resistance of the fibrous non-woven fabric 1 is improved.

In the step IV, the fibrous web 102 cooled to the ambient temperature is rolled up as the resulting fibrous non-woven fabric 1.

Figure 3:
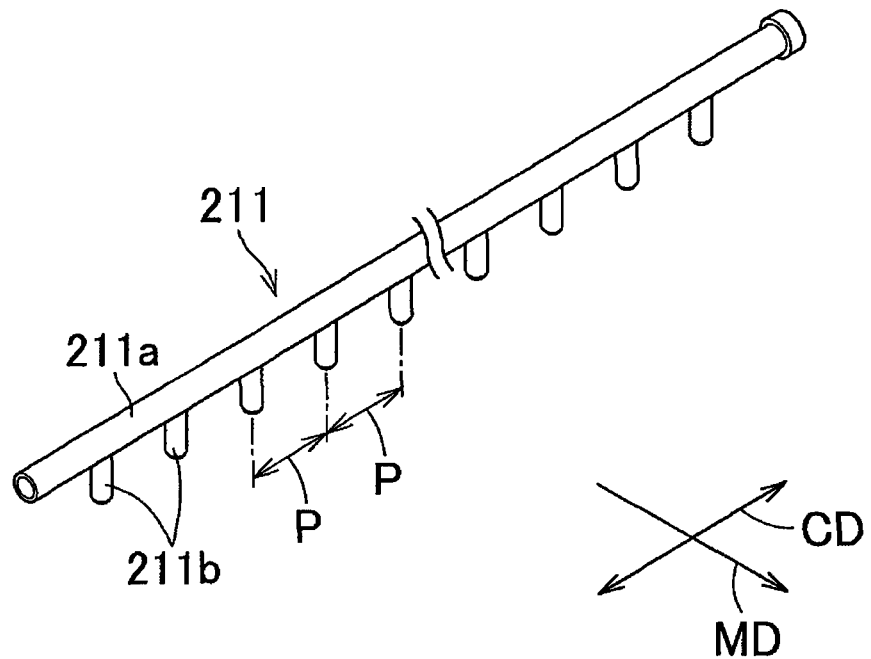
FIG. 3 is a perspective view showing a part of pneumatic piping.

Referring to FIG. 3 illustrating a perspective view of the first nozzle assembly 211, the first nozzle assembly 211 includes the first nozzle manifold 211a extending in parallel to the axial direction of the rotary suction drum 200, i.e., in the cross direction CD and a plurality of the first individual nozzles 211b provided to the first nozzle manifold 211a at the predetermined pitch. The respective first individual nozzles 211a are adapted to eject the hot air jets against the peripheral wall of the rotary suction drum 200. On the upstream of the first nozzle manifold 211a, there are provided a pressure regulation valve and an air heater (not shown). In the process illustrated in FIG. 2 adapted to obtain the fibrous non-woven fabric 1 of FIG. 1, the second and third stationary manifolds 212a, 213a and the second and third individual nozzles 212b, 213b are arranged in the same manner as the first manifold 211a and the first individual nozzles 211b of the first nozzle assembly 211. While the first, second and third nozzles 211b, 212b, 213b in the respective nozzle assemblies 211, 212, 213 are preferably of the uniform bore diameter and arranged at the same pitch in the cross direction CD, it is possible to set up the process of FIG. 2 to differentiate the bore diameter as well as the pitch among the first, second and third nozzle assemblies 211, 212, 213.

Figure 4:
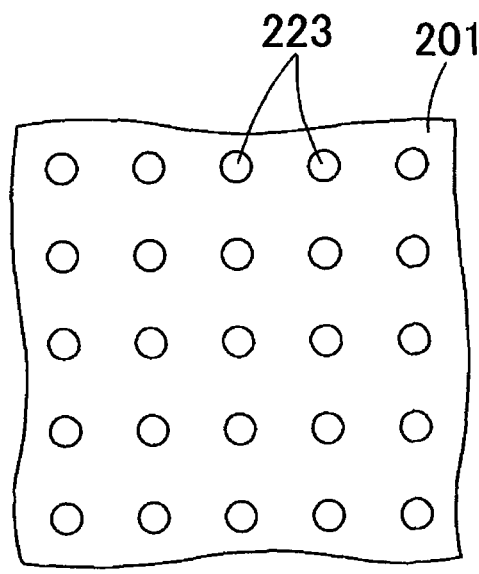
FIG. 4 is a fragmentary view of a metallic plate used to form a peripheral wall of a rotary suction drum.

Referring to FIG. 4 illustrating a fragmentary view of the metallic plate 201 used to form the peripheral wall of the rotary suction drum 200, the metallic plate 201 is formed with a plurality of perforations 223 in fluid-communication with the suction mechanism for the rotary suction drum 200. The respective perforations 223 have diameters, for example, in a range of 0.2 to 1 mm and arranged at a predetermined pitch in the circumferential direction and the axial direction of the rotary suction drum 200.

Figure 5:
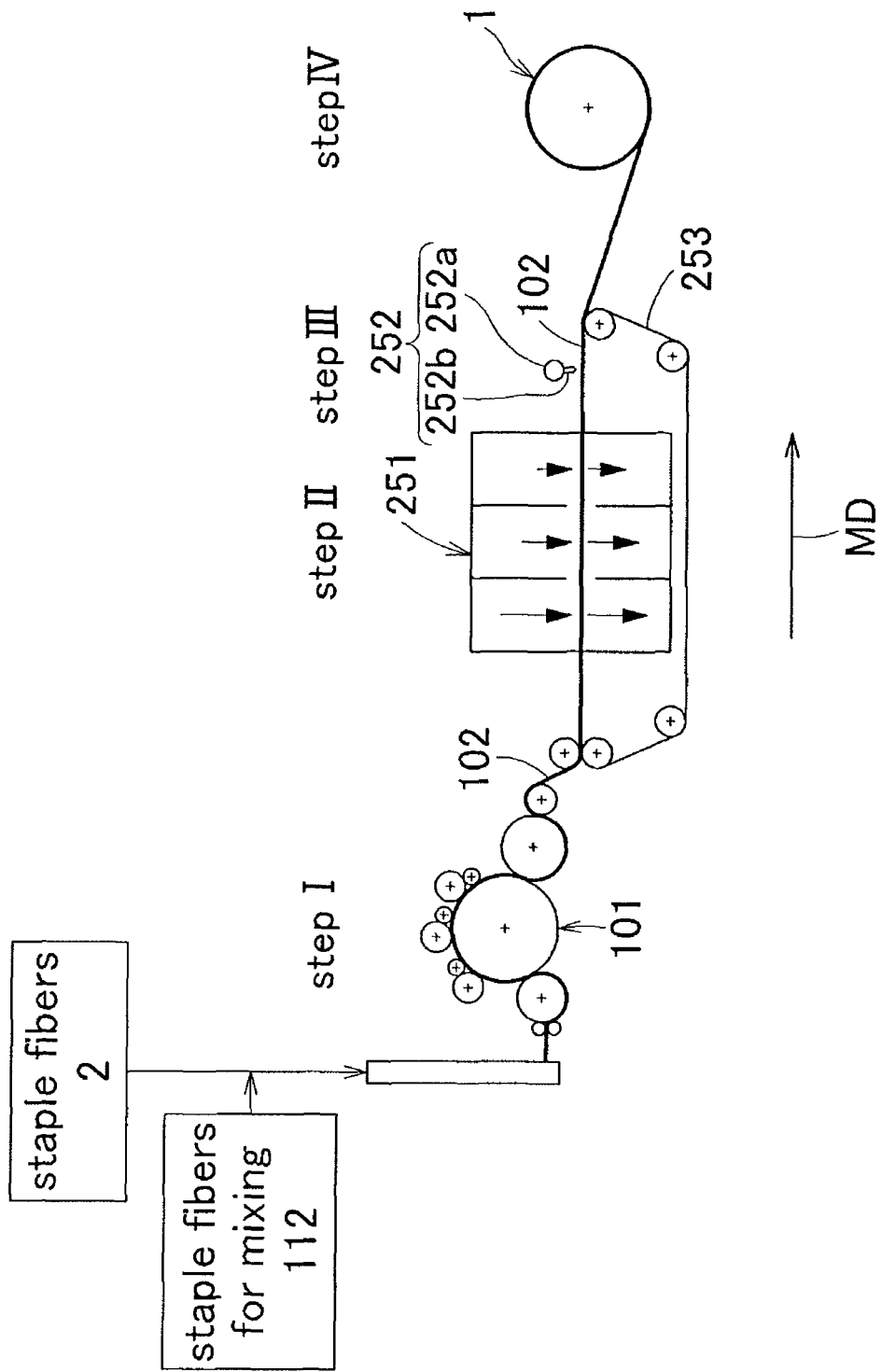
FIG. 5 is a diagram exemplarily illustrating another embodiment of a process for making the liquid-pervious fibrous non-woven fabric.

Referring to FIG. 5 showing a diagram similar to FIG. 2, it is exemplarily illustrating another embodiment of the process for making the liquid-pervious fibrous non-woven fabric 1. In the step I of FIG. 5, a mass of the staple fibers 2 is opened by the carding machine 101 to obtain the fibrous web 102. On the upstream of the carding machine 101, the appropriate staple fibers 112 for mixing may be mixed into the staple fibers 2. Preferably, the staple fibers 2 are mechanically crimped in advance to facilitate the opening treatment by the carding machine 101. The staple fibers 112 for mixing are the same as that in the process illustrated in FIG. 2.

In the step II of FIG. 5, the fibrous web 102 being transported by a mesh conveyor 253 is subjected, in a dryer 251, to hot air jets at a temperature sufficiently high to fuse the surfaces of the staple fibers 2 so that the staple fibers 2, 112 may be fused together and with the staple fibers 112 for mixing.

In the step III of FIG. 5, the fibrous web 102 still loaded on the mesh conveyor 253 and at a high temperature is now subjected to hot air jets at a predetermined temperature ejected from a plurality of nozzles 252b of a nozzle assembly 252 at a predetermined flow rate. The individual nozzles 252b are provided at a predetermined pitch to a stationary manifold 252a extending in a direction orthogonal to the machine direction MD i.e. in the cross direction CD and used to form the grooves 7 and the ridges 6 of the fibrous non-woven fabric 1. According to one embodiment of the nozzle assembly 252, the nozzles 252b are provided to the associated stationary manifold 252a at a pitch of 4 mm and have a bore diameter in a range of 0.5 to 2.5 mm.

In the step IV of FIG. 5, the fibrous web 102 cooled to the ambient temperature is rolled up as the fibrous non-woven fabric 1.

The mesh conveyor 253 used in the process of FIG. 5 is preferably of 18 to 30 mesh plain woven type. If the number of meshes is smaller than 18, it will be too coarse for the mesh conveyor and a trace of mesh wire will be left on the lower surface 4 of the fibrous non-woven fabric 1, making it difficult to smooth the lower surface 4. The number of meshes exceeding 30 will be too fine for the mesh conveyor and, in the step II as well as in the step III, it will be difficult for the hot air jets to permeate the fibrous web 102 and thereby it will be difficult to fuse the staple fibers 2 together in a desired manner on the lower surface of the fibrous web 102.

According to the process illustrated in FIG. 5, the fusion-bonding of the staple fibers 2, 112 together has already occurred in the step II. Therefore, it is easy for the step III to form the fibrous web 102 with the ridges 6 and the grooves 7 by the hot air jets ejected from the nozzle assembly 252. In other words, the first, second and third nozzle assemblies 211, 212, 213 used in the process of FIG. 2 to form the fibrous web 102 with the ridges 6 and the grooves 7 can be replaced by only one nozzle assembly 252 in the process of FIG. 5. In addition, the hot air jets ejected from the nozzle assembly 252 may be regulated, for example, its flow rate may be reduced to a range of 5.0 to 12.0 Nl/m$^2$ and/or its temperature may be set to a level lower than 200° C.

According to the findings of the inventors with respect to the fibrous non-woven fabric 1 obtained by employing the processes exemplarily illustrated in FIGS. 2 and 5, the staple fibers 2 extend across at least one ridge 6 to the respective bottoms 12 of the grooves 6 on both sides of the at least one ridge 6. On the respective bottoms 12, the staple fibers 2 are fused together or fused with the staple fibers 112 for mixing so as to restrict fluffing of these staple fibers 2, 112 on the upper surface 3 as will be apparent from the result of rubbing test described later. During this rubbing test, rubbing tried on the upper surface 3 primarily acts on each apex 11 of each ridge 6 and the vicinity thereof. However, it was found that fluffing on the apices 11 is substantially restricted for the reason that the staple fibers 2 constituting the apices 11 extend to the respective bottoms of the adjacent grooves 7 wherein these staple fibers 2 are fused together and with the staple fibers 112 for mixing.

Gradually varying the air flow rate of the hot air jets ejected from the third nozzle assembly 213 of FIG. 2 at a fixed temperature thereof, it was found that the possibility to restrict an occurrence of fluffing becomes more and more reliable as the air flow rate increases and thereby the grooves 7 become deeper, in other words, as the thickness t shown in FIG. 1 more and more decrease. Particularly in the fibrous non-woven fabric 1 in which the thickness t in the grooves 7 is 60% or less of the thickness T, the possibility of fluffing is restricted to a degree acceptable to be used as the top-sheet for disposable diapers or menstruation napkins. However, it should be noted that, in the grooves 7, the density increases and the specific volume decreased as the thickness t decreases, i.e., the depth increases in the bottom 12. If the fibrous non-woven fabric 1 formed with the grooves 7 each having an unacceptably small specific volume is used as the top-sheet for menstruation napkins, viscous bodily fluids such as menstrual blood can not be rapidly absorbed by the core through the bottoms 12 of the groove 7 and often stay behind on and in the bottoms 12 and the wearer's skin might be soiled with menstrual blood and/or menstrual blood staying behind on the top-sheet is uncomfortably visible when the used menstruation napkins are discarded. In view of such problem, the present invention should restrict the area on the surface of the fibrous non-woven fabric 1 possibly occupied by bodily fluids staying behind. To this purpose, the thickness t corresponding to the height measured from the lower surface 4 to the bottom 12 of each groove 7 is maintained at a level of 40% or more of the thickness T corresponding to the height measured from the lower surface 4 to the apex 11 of each ridge 6.

EXAMPLES

As Examples of the fibrous non-woven fabric, multiple types of the fibrous non-woven fabric with the ratio of the thickness T of each ridge 6 versus the thickness t of each groove 7 having been varied were made. Artificial menstrual blood was used as bodily fluids to evaluate the area of the upper surface 3 inclusive of the grooves 7 occupied by bodily fluids staying behind thereon and the rub resistance of the upper surface 3. Comparative examples of the fibrous non-woven fabric were prepared and the area of the upper surface occupied by bodily fluids staying behind thereon and the rub resistance of the upper surface were evaluated for these Comparative Examples as well. The evaluation result is indicated by TABLES 1 through 4. Measuring procedures for the thickness T and the thickness t of the fibrous non-woven fabric 1 having the ridges 6 and the grooves 7 and for the area of the fibrous non-woven fabric 1 over which bodily fluids stay behind thereon, and evaluating procedure for the rub resistance of the fibrous non-woven fabric will be described below in details.

(Measuring Procedures for Thickness T and Thickness t)

FIG. 6(a) and FIG. 6(b) are photographs respectively showing cross sections of the fibrous non-woven fabric piece taken along the cross direction CD and the measuring procedures for the thickness will be described with reference to these photographs.

1. Replacement blade HA-100B dedicated for a cutter knife HA-7NB (Trade Name) of Kokuyo Co., Ltd. is used to cut the fibrous non-woven fabric piece of thickness measurement in parallel to the cross direction CD and thereby to obtain a cross section for observation. Then, the fibrous non-woven fabric piece is placed on a horizontal surface H and Keyence's digital microscope VHX-100 is used to obtain a 25-fold photograph of the cross section for observation (See FIG. 6(a)).

2. Image analysis software USB Digital of Scalar Corporation is used as an image processing software to process the photographs of cross section and to binarize the image with a threshold value=50. For analysis of this binarized image shape, a computing method so-called "full up (ANAUZUME)" is employed and then "white" is selected as an object color and processed. In a similar manner, the computing method so-called "full up" is employed for analysis of the binarized image shape and then "black" is selected as an object color and processed. In the completely processed image, staple fibers fluffing outward from island-shaped white regions are erased to obtain a modified photograph (See FIG. 6(b)) of the CD cross sectional having no fluffing.

3. In the modified photograph, the line extending between the apices of adjacent ridges and a horizontal line R extending in parallel to the horizontal plane H in contact with the bottom of the groove are sought.

4. A vertical line Q being perpendicular to the horizontal plane H and extending upward through the bottom of the groove until it intersects the line S is sought.

5. Along the vertical line Q, a distance from the horizontal plane H to a point at which the vertical line Q intersects with the line S is determined as respective heights (thickness) T of the adjacent ridges. Along the vertical line Q, a distance from the horizontal plane H to a point at which the vertical line Q intersects with the horizontal line R as a thickness t of the groove (See FIG. 6(b)).

(Method for Measuring the Area Occupied by Bodily Fluids Staying Behind)

The method for measuring the area occupied by bodily fluids staying behind sequentially carried as follow:

1. 5 cm×5 cm fibrous non-woven fabric pieces are prepared as specimens for measurement.

2. Paper filter exclusively for viscous liquid No. 60 available from ADVANTEC MFS, INC. is cut into 10 cm×10 cm paper filter pieces and the 5 cm×5 cm fibrous non-woven fabric piece as specimen for measurement is placed on a stack of 20 paper filter pieces.

3. Using 10 cc pipette (digital micro-pipette for liquid handling NPX-10ML of Nichiryo Co., Ltd.), 2 cc of artificial menstrual blood as bodily fluids is slowly dropped onto the specimen for measurement.

Composition of artificial menstrual blood:
(1) ion-exchanged water: 1 liter
(2) glycerin: 80 g
(3) sodium carboxymethylcellulose: 8 g
(4) sodium chloride: 10 g
(5) sodium hydrogen carbonate: 4 g
(6) red No. 102: 8 g
(7) red No. 2: 2 g
(8) yellow No. 5: 2 g 4. 20 seconds after the drop treatment has been completed, the specimen is demounted from the stack of paper filter pieces and then air-dried.

5. After artificial menstrual blood in and on the specimen has been dried, a digital scanner (Image-scanner GT8700 of Seiko Epson Corporation) is used to scan a state of the amount of artificial menstrual blood staying in and on the specimen and to obtain an image thereof. (scanning parameter: color condition is set to True color-24 bits and pixel size is set to 59 pixels/cm.) (See FIG. 7).

6. The image obtained in the step 5 is processed by the image analysis software USB Digital of Scalar Corporation to binarize the image. The number of pixels colored in red by the artificial menstrual blood is stored as data on the basis of which the number of these pixels is converted to an area.

7. Parameters for binarization in the step 6 (a)re set to values as follows: threshold value=160; the number of extracted pixels=3 pixels or more; and range of extraction=400 pixels×400 pixels.

8. The number of pixels (image elements) and the areas converted therefrom are determined on the basis of three (3) specimens having the same t/T value and an average of the areas is obtained as "the area occupied by bodily fluids staying behind ($mm^2$) (See FIG. 7).

(Evaluating Method for Fastness to Rubbing)

A method for evaluating the fastness to rubbing includes the steps of:

1. Except the steps 2 through 7, the evaluation is carried out pursuant to JIS L 0844:2004 "Test method for dye fastness against rubbing".

2. As a tester, rubbing tester Model II (GAKUSHIN-type) as indicated below is used:

GAKUSHIN-type Color Fastness Rubbing Tester AB-301 of TESTER SANGYO CO. LTD.

3. Load during rubbing: 2N (200 gf)

4. Surface of rubbing member: cotton shirting No. 3 (pursuant to JIS L 0803)

5. The number of reciprocal rubbing motions: 20/min. Such rubbing motion is carried out for one minute at this rate.

6. Test specimen: A test piece is obtained by cutting the fibrous non-woven fabric to have a dimension in the longitudinal direction (i.e., machine direction) of 220 mm and to have a dimension in the transverse direction (cross direction) of 30 mm. This test piece is set to the tester so that the upper surface thereof formed with the ridges may face upward and the rubbing member may reciprocate in the longitudinal direction.

7. On the basis of observing the upper surface of the fibrous non-woven fabric after the rubbing test, the result is ranked as will be described. The fibrous non-woven fabric ranked as A, B and C can be used as the top-sheet:

A: No fluffing is observed.
B: Substantially no fluffing is observed.
C: The ridge having fluffing and the ridge having no fluffing are observed.
D: Significant fluffing is observed and some fluffs are observed to connect each pair of the adjacent ridges.

Examples 1 Through 10

1. First and second conjugate staple fibers both of core-in-sheath type were mixed together to obtain respective component staple fibers use to form these Examples 1 through 10 of the fibrous non-woven fabric. In these conjugate staple fibers, the core component was formed of polyester resin and the sheath component was formed of polyethylene resin. The first conjugate staple fiber has fineness of 2.2 dtex, fiber length of 45 mm and a mass of 80% by mass per unit area of the staple fiber as a whole. The second conjugate staple fiber has fineness of 2.6 dtex, fiber length of 38 mm and a mass of 20% by mass of the staple fibers as a whole. The mixed first and second staple fibers was treated by a roller card to obtain fibrous webs having masses of 15 $g/m^2$, 25 $g/m^2$, 35 $g/m^2$ and 40 $g/m^2$, respectively.

2. These fibrous webs were subjected to the step II illustrated in FIG. 2. Respective operating conditions in the step II of FIG. 2 for the first, second and third nozzles were set as follows:

(The First and Second Nozzles)
Air temperature at the nozzle manifold: 200° C.
Hot air ejection quantity per unit area of the fibrous web: 8.16 $Nl/m^2$ (The Third Nozzle Assembly)

Air temperature at the nozzle manifold: 350° C.

Hot air ejection quantity per unit area of the fibrous web: 10.92 to 19.17 Nl/m²

The individual nozzles of the respective nozzles were arranged at a pitch 4 mm in the cross direction to come into lines with the individual nozzles of the adjacent nozzles in the machine direction. The peripheral wall of the rotary suction drum was formed with a plurality of perforations at a percentage open area of 22.16%.

3. The fibrous webs were transported from the step II to the step III in which the fibrous webs were put in contact with hot air jets at a temperature of 135° C. for 5 minutes so that the staple fibers may be fused together and then the fibrous webs were cooled to the ambient temperature to obtain Examples 1 through 10 of the fibrous non-woven fabric.

Examples 1 through 10 of the fibrous non-woven fabric were evaluated as indicated in TABLES 1 through 3.

The specific volumes of the ridge and the groove referred to in TABLES 1 through 3 and TABLE 4 were determined by procedures (1) and (2) as follows:

(1) Based on the average mass calculated from 10 sheets of the fibrous non-woven fabric piece sized in 10 cm×10 cm, a mass/m² is determined according to the following equation:

$$\text{Mass}(g/m^2) = (\text{average mass}(g)) \div 0.01$$

It should be appreciated here that the fibrous non-woven fabric pieces each sized to be smaller than 10 cm×10 cm may be used without departing from the scope of the invention to determine the mass/m².

(2) With respect to the fibrous non-woven fabric piece, the thickness T from the lower surface to the apex of the ridge and the thickness t from the lower surface to the bottom of the groove are measured and the specific volume is determined according to the following equation:

Specific volume (cc/g) of the ridge or the groove = {(thickness T of the ridge or thickness t of the groove)×1000}÷mass (g/m²)

Comparative Examples 1 Through 18

Except that the hot air ejection quantity from the third nozzle assembly in FIG. 2 was set to a range of 8.17 to 24.58 Nl/m², the same conditions as those employed by Examples were employed to obtain Comparative Examples 1 through 18 of the fibrous non-woven fabric. Evaluation and ranking were also carried out in the same manner as in Examples. Result of evaluation was as indicated in TABLES 1 through 4.

As will be apparent from TABLES 1 through 4:

(1) Under the condition that the mass is in a range of 15 to 35 g/m² and at the same time the thickness ratio is in a range of 40 to 60%, the area of the fibrous non-woven fabric occupied by bodily fluids staying behind is relatively small. Specifically, viscous artificial menstrual blood used as bodily fluids smoothly permeates the fibrous non-woven fabric without significantly dispersing over the fibrous non-woven fabric and is rapidly transferred to filter paper used as an alternate for the absorbent structure.

(2) Comparative Examples of the fibrous non-woven fabric exhibiting t/T higher than 60% has a low rubbing resistance and is rather apt to fluff. The fibrous non-woven fabric exhibiting t/T of 60% or lower is relatively free from the possibility of fluffing.

(3) Concerning the specific volume of the fibrous non-woven fabric, under the condition that the specific volume of the ridge is in a range of 70 to 105 cc/g and at the same time the specific volume of the groove is in a range of 40 to 60 cc/g, viscous bodily fluids would not stay behind and the fibrous non-woven fabric would not readily fluff due to rubbing.

TABLE 1

| Mass 15 g/m² | Ex. 1 | Ex. 2 | Ex. 3 | Ex. 4 | Comp. Ex. 1 | Comp. Ex. 2 | Comp. Ex. 3 |
|---|---|---|---|---|---|---|---|
| Ejection quantity from the 3rd nozzle assembly (Nl/m²) | 10.92 | 13.67 | 16.42 | 19.17 | 8.17 | 21.83 | 24.58 |
| Specific volume of ridge(cc/g) | 99.8 | 98.0 | 97.0 | 103.3 | 100.2 | 103.3 | 109.5 |
| Specific volume of groove(cc/g) | 59.0 | 57.0 | 56.3 | 54.0 | 65.7 | 33.9 | 23.0 |
| t/T (%) | 59.1 | 58.2 | 58.0 | 52.3 | 65.6 | 32.8 | 21.0 |
| Area occupied by body fluid staying behind(mm²) | 12.1 | 10.1 | 9.8 | 19.1 | 22.2 | 131.5 | 453.1 |
| Result of rubbing test | C | B | B | B | D | B | A |

TABLE 2

| Mass 25 g/m² | Ex. 5 | Ex. 6 | Ex. 7 | Comp. Ex. 4 | Comp. Ex. 5 | Comp. Ex. 6 | Comp. Ex. 7 |
|---|---|---|---|---|---|---|---|
| Ejection quantity from the 3rd nozzle assembly (Nl/m²) | 10.92 | 13.67 | 16.42 | 8.17 | 19.17 | 21.83 | 24.58 |
| Specific volume of ridge (cc/g) | 86.2 | 96.3 | 91.5 | 87.1 | 92 | 82.9 | 85.5 |
| Specific volume of groove (cc/g) | 44.8 | 47.3 | 41 | 54.4 | 32.4 | 19.5 | 15 |
| t/T (%) | 52 | 48.8 | 44.8 | 62.1 | 35.2 | 23.6 | 17.7 |
| Area occupied by body fluid staying behind (mm²) | 22.5 | 20.1 | 19.9 | 26.2 | 36.7 | 49.3 | 128.7 |

TABLE 2-continued

| Mass 25 g/m² | Ex. 5 | Ex. 6 | Ex. 7 | Comp. Ex. 4 | Comp. Ex. 5 | Comp. Ex. 6 | Comp. Ex. 7 |
|---|---|---|---|---|---|---|---|
| Result of rubbing test | C | B | A | D | A | A | A |

TABLE 3

| Mass 35 g/m² | Ex. 8 | Ex. 9 | Ex. 10 | Comp. Ex. 8 | Comp. Ex. 9 | Comp. Ex. 10 | Comp. Ex. 11 |
|---|---|---|---|---|---|---|---|
| Ejection quantity From the 3rd nozzle assembly (Nl/m²) | 10.92 | 13.67 | 16.42 | 8.17 | 19.17 | 21.83 | 24.58 |
| Specific volume of ridge (cc/g) | 76.9 | 74.1 | 70.4 | 70.4 | 65.7 | 67.5 | 55.2 |
| Specific volume of groove (cc/g) | 45.2 | 42.0 | 40.0 | 42.7 | 33.8 | 21.7 | 13.4 |
| t/T (%) | 58.8 | 56.7 | 56.8 | 60.7 | 51.4 | 32.1 | 24.3 |
| Area occupied by body fluid staying behind (mm²) | 33.5 | 32.5 | 34.3 | 39.1 | 50.9 | 60 | 101.2 |
| Result of rubbing test | C | B | A | D | A | A | A |

TABLE 4

| Mass 40 g/m² | Comp. Ex. 12 | Comp. Ex. 13 | Comp. Ex. 14 | Com. Ex. 15 | Comp. Ex. 16 | Comp. Ex. 17 | Comp. Ex. 18 |
|---|---|---|---|---|---|---|---|
| Ejection quantity From the 3rd nozzle assembly (Nl/m²) | 8.17 | 10.92 | 13.67 | 16.42 | 19.17 | 21.83 | 24.58 |
| Specific volume of ridge (cc/g) | 64.6 | 58.7 | 59.0 | 61.0 | 59.9 | 57.5 | 55.4 |
| Specific volume of of groove (cc/g) | 42.4 | 34.5 | 30.3 | 28.9 | 28.5 | 20.3 | 12.1 |
| t/T (%) | 65.6 | 58.8 | 51.4 | 47.4 | 47.6 | 35.3 | 21.8 |
| Area occupied by body fluid staying behind (mm²) | 98 | 80.8 | 81.2 | 77.2 | 80.9 | 298.3 | 803.3 |
| Rubbing test Result | C | B | A | A | A | A | A |

Figure 7:
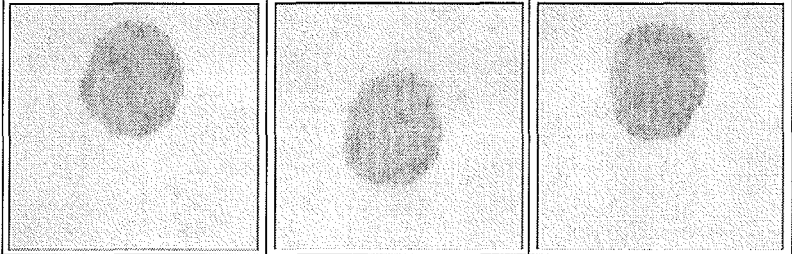
FIG. 7 is a diagram exemplarily showing states in which bodily fluids may stay behind.

FIG. 7 is a diagram exemplarily illustrating procedures to measure an area occupied by bodily fluids staying behind on and in the fibrous non-woven fabric on the basis of Example 7 and Comparative Example 7 of the fibrous non-woven fabric. More specifically, FIG. 7 shows images of bodily fluids staying behind on and in these Examples of the fibrous non-woven fabric, results obtained by binarizing these images, the number of pixels and the area obtained from the result of binarization, and the average number of pixels and the average area.

| {Reference Signs List} | |
|---|---|
| 1 | fibrous non-woven fabric |
| 2 | staple fibers |
| 3 | upper surface |
| 4 | lower surface |
| 6 | ridge |
| 7 | groove |

| {Reference Signs List} | |
|---|---|
| 11 | apex |
| 12 | bottom |
| A | longitudinal direction |
| B | transverse direction |
| C | thickness direction |
| P | pitch |
| T | thickness of apex |
| t | thickness of bottom |

The invention claimed is:

1. A liquid-pervious fibrous non-woven fabric having a longitudinal direction, a transverse direction and a thickness direction being orthogonal to one another, said liquid-pervious fibrous non-woven fabric comprising:

upper and lower surfaces opposed to each other in the thickness direction and both extending in the longitudinal direction and the transverse direction, the upper surface being formed with ridges and grooves extending in parallel in the longitudinal direction to be alternately arranged in the transverse direction, and the lower surface being substantially flat; and staple fibers, made of thermoplastic synthetic resin, being fused together in the liquid-pervious fibrous non-woven fabric, wherein:

a thickness t measured from the lower surface to a bottom of one of the grooves is in a range of 40 to 60% of a thickness T measured from the lower surface to an apex of one of the ridges, the staple fibers include fibers each having a fiber length sufficiently long to extend across at least one ridge of the ridges to the grooves on both sides of the at least one ridge, and a specific volume of one of the ridges is greater than a specific volume of one of the grooves.

2. The liquid-pervious fibrous non-woven fabric defined by claim 1, wherein the staple fibers extending across the ridges are fused, in each of the grooves adjacent to the ridge, with staple fibers of a different type from the staple fibers extending across the ridges.

3. The liquid-pervious fibrous non-woven fabric defined by claim 1, wherein the liquid-pervious fibrous non-woven fabric has a mass per unit square meter in a range of 15 to 35 g/m².

4. The liquid-pervious fibrous non-woven fabric defined by claim 1, wherein the specific volume of said one of the ridges is in a range of 70 to 105 cc/g and the specific volume of said one of the grooves is in a range of 40 to 60 cc/g.

5. The liquid-pervious fibrous non-woven fabric defined by claim 1, wherein the staple fibers comprise staple fibers each having an apparent fiber length in a range of 10 to 80 mm.

6. A method of manufacturing a liquid-pervious fibrous non-woven fabric having a longitudinal direction, a transverse direction and a thickness direction being orthogonal to one another, said liquid-pervious fibrous non-woven fabric comprising:

upper and lower surfaces opposed to each other in the thickness direction and both extending in the longitudinal direction and the transverse direction, the upper surface being formed with ridges and grooves extending in parallel in the longitudinal direction to be alternately arranged in the transverse direction, and the lower surface being substantially flat; and staple fibers, made of thermoplastic synthetic resin, being fused together in the liquid-pervious fibrous non-woven fabric, wherein:

a thickness t measured from the lower surface to a bottom of one of the grooves is in a range of 40 to 60% of a thickness T measured from the lower surface to an apex of one of the ridges, the staple fibers include fibers each having a fiber length sufficiently long to extend across at least one ridge of the ridges to the grooves on both sides of the at least one ridge, and a specific volume of one of the ridges is greater than a specific volume of one of the grooves, said method comprising:

compressing a fibrous web containing a given mass/m² of the staple fibers under an ejection pressure of first hot air jets until a thickness of the fibrous web is reduced to ½ to ¼ of an initial thickness of the fibrous web; and then forming the ridges and the grooves by subjecting the fibrous web to second hot air jets ejected from second nozzles arranged in a cross direction orthogonal to a machine direction while the fibrous web is continuously transported in the machine direction so that each of the ridges is formed directly below a space defined between each pair of adjacent second nozzles and each of the grooves is formed directly below one of the second nozzles.

7. The method defined by claim 6, wherein said first hot air jets are ejected from first nozzles to the fibrous web to compress the fibrous web.

8. The method defined by claim 7, wherein said first nozzles are disposed upstream of said second nozzles in the machine direction.

9. The method defined by claim 7, wherein the ejection pressure of the first hot air jets ejected from said first nozzles is different from that of the second hot air jets ejected from said second nozzles.

10. The method defined by claim 7, wherein a temperature of the first hot air jets ejected from said first nozzles is different from that of the second hot air jets ejected from said second nozzles.

11. The method defined by claim 7, wherein the first hot air jets ejected from said first nozzles render smooth a surface of the fibrous web facing the first nozzles, before the grooves and ridges are formed in the smooth surface of the fibrous web by the second hot air jets ejected from second nozzles.

* * * * *